United States Patent [19]

Calderó Ges et al.

[11] Patent Number: 4,539,331

[45] Date of Patent: Sep. 3, 1985

[54] IMIDAZOLE CARBOXAMIDE DERIVATIVES AND PHARMACEUTICAL COMPOSITIONS THEREOF

[75] Inventors: José M. Calderó Ges; Antonio P. Dueña, both of Barcelona, Spain

[73] Assignee: Laboratorios Vita, S.A., Barcelona, Spain

[21] Appl. No.: 581,651

[22] Filed: Feb. 21, 1984

Related U.S. Application Data

[63] Continuation of Ser. No. 330,960, Dec. 15, 1981, abandoned.

[30] Foreign Application Priority Data

Apr. 16, 1981 [ES] Spain ................................. 502162

[51] Int. Cl.$^3$ .................. A61K 31/415; C07D 233/90
[52] U.S. Cl. ..................................... 514/400; 548/343
[58] Field of Search ..................... 548/343; 424/273 R

[56] References Cited

FOREIGN PATENT DOCUMENTS 140966 9/1980 Fed. Rep. of Germany.
101373 9/1978 Japan.

OTHER PUBLICATIONS

Honda et al, *Chemical Abstracts*, vol. 90, (1979), No. 72189z.
Creuzburg et al, *Chemical Abstracts*, vol. 94, (1981), No. 151,893k.

*Primary Examiner*—Robert W. Ramsuer
*Attorney, Agent, or Firm*—Bell, Seltzer, Park & Gibson

[57] ABSTRACT

Imidazole derivatives having the formula:

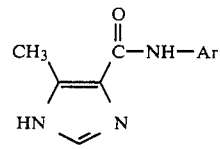

Ar is a benzene ring substituted by one or more of the following groups, alone or in combination: halogen, $C_1$–$C_6$ alkyl, $C_1$–$C_6$ alkoxy, trifluoromethyl, and nitro, a process for the preparation thereof and an antiinflammatory, analgesic and antipyretic pharmaceutical composition containing them as active substance are disclosed.

15 Claims, No Drawings

IMIDAZOLE CARBOXAMIDE DERIVATIVES AND PHARMACEUTICAL COMPOSITIONS THEREOF

This application is a continuation of application Ser. No. 330,960, filed Dec. 15, 1981 now abandoned.

FIELD OF THE INVENTION

This invention relates to new imidazole derivatives having an antiinflammatory, analgesic and antipyretic action and being free from gastric irritation activity, and to processes for the preparation of such derivatives and for the formation of therapeutically useful pharmaceutical compounds.

SUMMARY OF THE INVENTION

The invention provides compounds having the general formula (I)

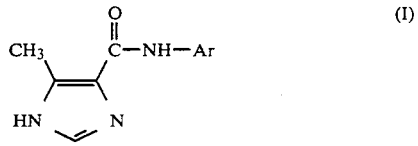

and physiologically acceptable salts thereof, wherein Ar is a benzene ring substituted by one or more of the following groups, alone or in combination: halogen, $C_1$-$C_6$ alkyl, $C_1$-$C_6$ alkoxy, trifluoromethyl, and nitro.

The alkyl or alkoxy groups may be straight or branched chain.

Among the physiologically acceptable salts there are those formed with inorganic acids such as the hydrochloride, hydrobromide, sulphate or organic mono- and dicarboxylic acids such as the acetate, maleate, fumarate, etc.

The compounds and the salts thereof may be administered orally or parenterally, topically or as suppositories, oral administration being preferred.

In the pharmaceutical compositions they are accompanied generally by appropriate carriers. The pharmaceutical forms for oral administration may be capsules, tablets or syrups; for topical application they may be sprays ointment, lotion or creams.

The daily dosage used for oral or rectal administration is from 5 mg to 100 mg of active substance per kg body weight, administered as unit dose portions of 50 to 1000 mg, the most regular dosage lying between 7 mg and 70 mg/kg body weight/day.

The compositions for topical application generally contain from 2% to 20% by weight of active substance, the number of applications depending on the intensity of the pain picture.

The compounds may be associated with other therapeutical agents, specific conditions depending on the affection being treated.

The process for the preparation of the compounds of this invention consists of reacting a primary amine of the general formula Ar-$NH_2$ (II) wherein Ar has the same meaning as defined hereinbefore, with a compound of the general formula (III)

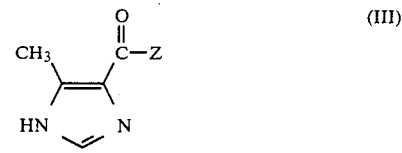

where Z is a reactant group such as halogen, O-COO$R_1$ ($R_1$ being a $C_1$-$C_8$ straight or branched chain alkyl group or a substituted or unsubstituted aryl group), isourea, dicyclohexylisourea, O$R_2$ ($R_2$ being a $C_1$-$C_3$ alkyl groups), in an appropriate solvent medium, to effect the amide bond.

The chemical reaction taking place in this process may be represented by the following scheme:

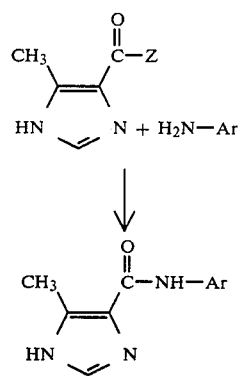

When Z is halogen, e.g. chlorine, the general compound of formula (III) is 5-methyl-4-imidazolecarbonyl chloride which may be prepared from 5-methyl-4-imidazolecarboxylic acid by any of the conventional methods using thionyl chloride, phosphorus pentachloride or the like as chlorination reactants.

In the copulation with the aromatic amine (II) it is advisable to use the acid chloride hydrochloride in an appropriate solvent medium such as chloroform, benzene, toluene, ethyl ether, etc., in a mole ratio of 1:1 of the stoichiometric reaction.

The process is conducted at temperatures lying between −10° C. and the boiling point of the solvent used, the 50°-80° range being advisable.

The buffering of the hydrochloric acid in the process is effected with a tertiary amine, such as triethylamine, when an exclusively organic reaction medium is used, or an inorganic base such as sodium carbonate when water is present.

The product obtained may be purified normally by crystallisation in a solvent, e.g. a lower alcohol or a ketone.

When Z is —OCOO$R_1$, the general compound of formula (III) is the mixed anhydride obtained by reacting the 5-methyl-4-imidazolecarboxylic acid with a compound of the general formula X—CO—O—$R_1$ where X is halogen and $R_1$ is a $C_1$-$C_8$ alkyl group (straight or branched chain) or an aryl group (substituted or not) in an inert solvent medium, in presence of a tertiary amine, the intermediate mixed anhydride thus formed being reacted thereafter "in situ" with the aromatic amine (II).

When Z is an isourea group, the general compound of formula (III) is the reaction product of the 5-methyl-4-imidazolecarboxylic acid with a carbodiimide and the reaction with the aromatic amine (II) is effected in a mole ratio of 1:1, in an appropriate reaction medium such as tetrahydrofurane, acetonitrile or mixtures thereof.

The following Examples are given as an illustration of the invention and are not intended to be limitations thereof:

EXAMPLE 1

(a) To a suspension of 880 g (5.4 moles) of 5-methyl-4-imidazolecarboxylic acid hydrochloride in 100 ml of dimethylformamide and 2 liters of toluene at 60° C., there was added slowly over 2 hours 790 ml (10.8 moles) of thionyl chloride. At the end of the addition, the mixture was held with good stirring for 1 hour at 80° C. It was allowed to cool, filtered, the solid was washed with 1 liter of toluene. 685 g of 5-methyl-4-imidazolecarbonyl chloride hydrochloride were obtained.

(b) To a solution of 425 g (3 moles) of 3-chloro-4-methylaniline in 3 liters of toluene, there was added slowly with vigorous stirring 560 g (3.1 moles) of the product obtained in (a). At the end of the addition, the mixture was heated to 80° C. for 1 hour, with continuous stirring. The mixture was allowed to cool to room temperature and a concentration solution of sodium carbonate in water was added to pH 9 to 10. The solid precipitate was filtered, washed with 1 liter of water and dried in a stove at 50° C. 689 g of N-(3-chloro-4-methylphenyl)-5-methyl-4-imidazolecarboxamide were obtained.

The above crude product was dissolved in 3.5 liters of isopropyl alcohol, was decoloured with activated carbon, was filtered and concentrated to dryness. 644 g (86% yield) of N-(3-chloro-4-methylphenyl)-5-methyl-4-imidazolecarboxamide were obtained. The product is white crystalline, m.p. 215°–217° C., insoluble in water and toluene, sparingly soluble in an acid aqueous medium, moderately soluble in chloroform and soluble in methanol, ethanol, isopropanol and acetone.

Analysis gives the formula $C_{12}H_{12}ClN_3O$ (molecular weight=249.71).

% Calculated: C 57.72, H 4.84, N 16.83, Cl 14.20. % Found: C 57.69, H 4.85, N 16.80, Cl 14.21.

The product gives an absorption maximum at 268 nm in methanol solution in UV.

It gives the following bands in IR spectrum (KBr pad): 3340, 3150, 1660, 1595, 1515, 1440, 1390, 1380, 1310, 1240, 1090, 1040, 945, 920, 875, 825 cm$^{-1}$ among the most significant and characteristic.

EXAMPLE 2

To a solution of 740 g (5.22 moles) of 3-chloro-4-methylaniline and 1054.6 g (10.44 moles) of triethylamine in 10 liters of acetone at room temperature and vigorous stirring, there were added slowly 945 g (5.22 moles) of 5-methyl-4-imidazolecarbonyl chloride hydrochloride. After the addition was ended, the mixture was refluxed for 1 hour and then allowed to cool to room temperature and filtered. The liquid filtrate was evaporated until a slight precipitation appeared, it was then poured over 20 liters of cold water with stirring, filtered and the precipitate was dried to give N-(3-chloro-4-methylphenyl)-5-methyl-4-imidazolecarboxamide, a crude yellowish product. Crystallisation from isopropyl alcohol gave 1108 g (85% yield) of the desired pure product having the same characteristics as the one obtained in Example 1.

EXAMPLE 3

To a solution of 81 g (0.5 mole) of 5-methyl-4-imidazolecarboxylic acid hydrochloride and 160 g (1.58 moles) of triethylamine in 1000 ml of anhydrous acetone, previously cooled to 0° C., there were added over a period of about 5 minutes 105 ml (1 mole plus 5% excess) of ethyl chloroformate with good stirring. The mixture was allowed to stand for 15 minutes under these conditions. There were added slowly 70.5 g (0.5 mole of 3-chloro-4-methylaniline and the mixture was stirred for 1 hour at room temperature. Thereafter, a solution of 1N NaOH to pH 12–13 was added and the mixture was held at 40° C. for 1 hour. It was allowed to cool, the solution was poured over 1000 ml of cold water with good stirring, was filtered and the precipitated N-(3-chloro-4-methylphenyl)-5-methyl-4-imidazolecarboxamide was dried. Crystallisation from ispropyl alcohol gave 62 g (50% yield) of the desired pure product, having the same characteristics as the one described in Example 1.

EXAMPLE 4

To a solution of 32.5 g (0.2 mole) of 5-methyl-4-imidazolecarboxylic acid hydrochloride in 500 ml of anhydrous tetrahydrofurane, previously cooled to 0° C., there were added over a period of about five minutes 43.2 (0.21 mole) of dicyclohexylcarbodiimide with good stirring and it was allowed to rest for 15 minutes under these conditions. There were added in one shot 28.2 (0.2 mole) of 3-chloro-4-methylaniline and the mixture was stirred in a cold bath for 1 hour and thereafter for 3 hours at room temperature. 1000 ml of a solution of sodium carbonate (10% by weight) to pH 10–12 and 200 ml of toluene were added. The precipitated dicyclohexylurea was filtered out, the organic phase was decanted, concentrated to turbidity and cooled to 0° C. The N-(3-chloro-4-methylphenyl)-5-methyl-4-imidazolecarboxamide was precipitated out, filtered and dried. Crystallisation from isopropyl alcohol gave 15 g (30% yield) of the desired pure product, having the same characteristics as the one described in Example 1.

EXAMPLE 5

The following compounds are produced in a similar way from the corresponding aromatic amine by the processes described in Examples 1, 2, 3 and 4:

(a) N-(5-chloro-2-methoxyphenyl)-5-methyl-4-imidazolecarboxamide. m.p. 214°–216° C. I.R. spectrum: 3310, 3160, 1660, 1600, 1540, 1480, 1420, 1300, 1250, 1210, 1130, 1090, 1025, 945, 910, 875, 800, 650 cm$^{-1}$.

(b) N-(3-methyl-4-nitrophenyl)-5-methyl-4-imidazolecarboxamide. m.p. 273°–275° C. I.R. spectrum: 3300, 3100, 1690, 1585, 1525, 1495, 1450, 1320, 1245, 1080, 940, 840, 750, 650 cm$^{-1}$.

(c) N-(5-fluoro-2-methylphenyl)-5-methyl-4-imidazolecarboxamide. m.p. 232°–234° C. I.R. spectrum: 3350, 3250, 1635, 1600, 1530, 1450, 1310, 1200, 1150, 1115, 1000, 935, 870, 855, 805, 640 cm$^{-1}$.

(d) N-(2-trifluoromethylphenyl)-5-methyl-4-imidazolecarboxamide. m.p. 175°–177° C. I.R. spectrum: 3360, 3195, 1660, 1595, 1535, 1460, 1430, 1320, 1175, 1110, 1035, 940, 895, 800, 770, 655 cm$^{-1}$.

(e) N-(2,4,6-trimethylphenyl)-5-methyl-4-imidazolecarboxamide. m.p. 226°–228° C. I.R. spectrum: 3125, 3000, 1630, 1595, 1515, 1500, 1430, 1225, 1085, 1035, 945, 905, 850, 780, 660 cm$^{-1}$.

(f) N-(2-fluorophenyl)-5-methyl-4-imidazolecarboxamide. m.p. 195°–197° C. I.R. spectrum: 3350, 3250, 1650, 1600, 1520, 1400, 1320, 1250, 1190, 1085, 940, 885, 755, 650 cm$^{-1}$.

(g) N-(2-methoxyphenyl)-5-methyl-4-imidazolecarboxamide. m.p. 182°–184° C. I.R. spectrum: 3350, 3125, 1670, 1600, 1540, 1455, 1340, 1245, 1155, 1035, 1015, 820, 745 cm$^{-1}$.

(h) N-(4-chloro-3-nitrophenyl)-5-methyl-4-imidazolecarboxamide. m.p. 208°–210° C. I.R. spectrum: 3325, 3100, 1640, 1595, 1525, 1380, 1330, 1255, 1040, 920, 885, 830, 750, 660 cm$^{-1}$.

EXAMPLE 6

This example relates to the preparation of various pharmaceutical compositions containing the compound of Example 1, N-(3-chloro-4-methylphenyl)-5-methyl-4-imidazolecarboxamide as active substance.

(a) 1000 no O gelatine capsules were produced, each containing 250 mg of the compound (Example 1), previously compacted.

The composition was as follows:

|  | For 1000 capsules |
| --- | --- |
| Compound (Example 1) | 250 g. |
| Anhydrous lactose U.S.P. · | 120 g. |
| Corn starch | 20 g. |
| Silicon dioxide | 5 g. |
| Magnesium stearate | 200 mg. |

After sifting, the components were homogenously mixed and the resulting powder was put into the gelatine capsules in an appropriate filling machine.

(b) 1000 suppositories were produced, each contaning 250 mg of the compound (Example 1) using the following ingredients:

|  | For 1000 suppositories |
| --- | --- |
| Compound (Example 1) | 250 g. |
| Adeps solidus (DAB) | 1340 g. |

The active substance was sifted through a 100 μm aperture sieve and homogenously mixed with the previously molten adeps solidus. The mixture was formed in appropriate moulds to contain 250 mg of active substance per suppository.

(c) 1000 suppositories were produced, each containing 500 mg of the compound (Example 1), from the following ingredients:

|  | For 1000 suppositories |
| --- | --- |
| Compound (Example 1) | 500 g. |
| Adeps solidus | 2320 g. |

The active substance was sifted through a 100 μm aperture sieve and uniformly mixed with the previously molten adeps solidus. The mixture was formed in appropriate moulds to contain 500 mg of active substance per suppository.

(d) 1000 tablets were produced, each containing 250 mg of the compound (Example 1) from the following ingredients:

|  | For 1000 tablets |
| --- | --- |
| Compound (Example 1) | 250 g. |
| Corn starch | 123 g. |
| Gelatine | 10 g. |
| Microcrystalline cellulose | 60 g. |
| Silicon dioxide | 2 g. |
| Magnesium stearate | 5 g. |

After mixing the compound (Example 1) and the corn starch, the mix was kneaded with an aqueous solution of the gelatine. The mix was dried and granulated. First the microcrystalline cellulose and the silicon dioxide and then the magnesium stearate were incorporated into the mix. After homogenisation, the mix was compressed in a tablet forming machine to produce 1000 tablets, each containing 250 mg of active substance.

(e) 1000 tablets were produced, each containing 500 mg of the compound (Example 1), from the following ingredients:

|  | For 1000 tablets |
| --- | --- |
| Compound (Example 1) | 500 g. |
| Corn starch | 146 g. |
| Gelatine | 20 g. |
| Microcrystalline cellulose | 70 g. |
| Silicon dioxide | 4 g. |
| Magnesium stearate | 10 g. |

After mixing the compound (Example 1) and the corn starch, the mix was kneaded with an aqueous solution of the gelatine. The mix was dried and granulated. First the microcrystalline cellulose and the silicon dioxide and then the magnesium stearate were incorporated in the mix. After homogenisation, the mix was compressed in a tablet forming machine to produce 1000 tablets, each containing 500 mg of active substance.

(f) 1000 grams of ointment were produced, containing 5% of the compound (Example 1), from the following ingredients:

| Compound (Example 1) | 50 g. |
| --- | --- |
| White soft paraffin B.P. | 950 g. |

The compound (Example 1) is sifted through a 100 μm aperture sieve after grinding and is evenly mixed with the white soft paraffin, the mix being finally refined through an appropriate mill.

(g) 1000 grams of cream were produced, containing 5% of the compound (Example 1), from the following ingredients:

| Compound (Example 1) | 50 g. |
| --- | --- |
| Cetomacrogol emulsifying ointment, B.P. | 300 g. |
| Nipagin | 2,5 g. |
| Nipasol | 1,5 g. |
| Distilled water ad | 1000 g. |

The compound (Example 1) was sifted through a 100 μm aperture sieve and evenly mixed with the Cetomacrogol emulsifying ointment at 65° C. The nipagin and nipasol were dissolved in the warm water at 65° C. and this solution was then mixed with the oily mix of the active substance, with continuous stirring while cooling to form the cream.

(h) Ten liters of oral suspension were produced, containing 500 mg of compound (Example 1) per each 5 c.c. measure, from the following ingredients:

|  | For 10 liters |
| --- | --- |
| Compound (Example 1) | 1000 g. |
| Sorbitol solution (U.S.P.) | 2000 g. |
| Glycerine (U.S.P.) | 1000 g. |
| Nipagin | 15 g. |
| Nipasol | 2 g. |
| Polysorbate 80 (U.S.P.) | 10 g. |
| Carboxymethylcellulose | 100 g. |
| Sweetener and flavouring | required amount |
| Distilled water ad | 10 liters |

The sorbitol, glycerine, polysorbate 80, nipagin and nipasol were mixed together with gentle heating until the latter two substances were dissolved. The compound (Example 1) was dispersed in the above mix and homogenised through a colloid mill. The carboxymethylcellulose was swelled in a portion of water and added to the above portion. Finally the sweeteners and flavourings are added and the mix is made up to 10 liters.

EXAMPLE 7

The pharmaceutical compositions of Example 6 were prepared in a similar way using the corresponding compounds of Example 5.

PHARMACOLOGICAL DESCRIPTION

The compounds of the invention have mainly an anti-inflammatory, analgesic and antipyretic activity among other pharmacological activities; the toxicity thereof is very low and they have no appreciable irritant action on the gastric mucous.

1. Anti-inflammatory activity

The anti-inflammatory activity has been demonstrated in the rat with the carrageenin oedema method described by Winter et al, Proceedings of the Society for Experimental Biology and Medicine, 111, 544 (1962). The test results show an activity similar to that of phenylbutazone for the compound of Example 1.

| Product | Administration | $ED_{50}$ (mg/kg) (x) |
| --- | --- | --- |
| Example 1 | Oral | 60 |
| Example 5a | Oral | 78 |
| Phenylbutazone | Oral | 45 |
| Example 1 | i.p. | 16,5 |
| Phenylbutazone | i.p. | 18,5 |

Anti-inflammatory activity.
(x) ED = effective dose.

2. Analgesic activity

The analgesic activity was measured in the mouse with the writhing test orginally described by Van der Wende et al., Federal Proceedings, 15, 494 (1956) and modified by Koster et al., Federal Proceedings, 18, 412 (1959) and by Witkin et al., Journal of Pharmacology and Experimental Therapeutics, 133, 400 (1961). The test results show as analgesic action 1.5 times that of aspirin for the compound of Example 1.

| Product | Administration | $ED_{50}$ (mg/kg) |
| --- | --- | --- |
| Example 1 | i.p. | 30 |
| Example 5b | i.p. | 35 |
| Example 5c | i.p. | 50 |
| Example 5h | i.p. | 33 |
| Aspirin | i.p. | 45 |

Analgesic activity.

3. Antipyretic activity

The antipyretic activity was shown by measuring the beer yeast induced fever following the method described by Smith et al., Journal of Pharmacology and Experimental Therapeutics, 54, 346 (1935). The test results shown an antipyretic activity three times that of aspirin and slightly superior to that of pyramidon for the compound of Example 1.

| Product | Administration | $ED_{50}$ (mg/kg) |
| --- | --- | --- |
| Example 1 | Oral | 48 |
| Example 5b | Oral | 58 |
| Aspirin | Oral | 140 |
| Pyramidon | Oral | 55 |

Antipyretic activity.

4. Gastric tolerance

In the gastric tolerance test, the product was compared with aspirin and phenylbutazone on the rat, with oral administration. At dose levels of 1000 and 200 mg/kg, respectively, aspirin and phenylbutazone provoke haemorrhage spots, congestion and oedema, whereas the compound of Example 1 causes no alteration at the same dose levels.

5. Acute toxicity

The acute toxicity in the rat and mouse is low

| Species | Administration | $LD_{50}$ (mg/kg) (x) |
| --- | --- | --- |
| Rat | Oral | >12000 |
| Mouse | Oral | >8000 |
| Rat | i.p. | 560 |
| Mouse | i.p. | 700 |

Acute toxicity of the compound of Example 1.
(x) LD = Lethal dose.

What we claim is:
1. Imidazole derivatives of the general formula I

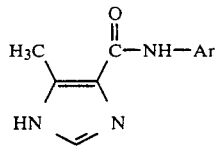

where Ar is a benzene ring substituted by one or more of the following groups, alone or in combination: halogen, $C_1-C_6$ alkyl, $C_1-C_6$ alkoxy, trifluoromethyl and nitro.

2. Imidazole derivatives according to claim 1, wherein the substituents in Ar are a halogen atom and a $C_1-C_6$ alkyl group.

3. Imidazole derivatives according to claim 1 wherein the substituents in Ar are a chlorine atom and a $C_1-C_6$ alkyl group.

4. Imidazole derivatives according to claim 1, wherein the substituents in Ar are a chlorine atom and a —$CH_3$ group.

5. Imidazole derivatives according to claim 1, wherein the substituents in Ar are $C_1-C_6$ alkyl groups.

6. Imidazole derivatives according to claim 1, wherein the substituents in Ar are 1 or 2 in number and located at the 3 and/or 4 position.

7. Imidazole derivatives having the structural formula:

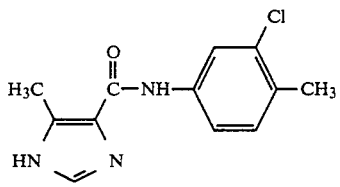

8. Physiologically acceptable acid addition salts of the imidazole derivatives of the general formula I as defined in claim 1.

9. A pharmaceutical composition with analgesic, antipyretic and antiinflammatory activity wherein the composition contains as active ingredient a therapeutically effective amount of one of the imidazole derivatives of the general formula I

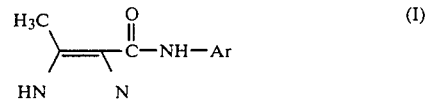

where Ar is a benzene ring substituted by one or more of the following groups, alone or in combination: halogen, $C_1-C_6$ alkyl, $C_1-C_6$ alkoxy, trifluoromethyl and nitro, associated with excipients and/or other pharmaceutically acceptable active substances.

10. A pharmaceutical composition according to claim 9, wherein the active substance is disposed in a suitable form for oral, parenteral, rectal administration or for topical applications.

11. A pharmaceutical composition according to claim 9, wherein in the imidazole derivatives of the general formula I, the substituents in Ar are a halogen atom and a $C_1-C_6$ alkyl group.

12. A pharmaceutical composition according to claim 9, wherein in the imidazole derivatives of the general formula I, the substituents in Ar are a chlorine atom and a $C_1-C_6$ alkyl group.

13. A pharmaceutical composition accordinag to claim 9, wherein in the imidazole derivatives of the general formula I, the substituents in Ar are a chlorine atom and a —$CH_3$ group.

14. A pharmaceutical composition according to claim 9, wherein in the imidazole derivatives of the general formula I, the substituents in Ar are a chlorine group located at 3 position and a —$CH_3$ group located at 4 position.

15. A pharmaceutical composition according to claim 9, wherein in the imidazole derivatives of the general formula I, the substituents in Ar are $C_1-C_6$ alkyl groups.

* * * * *